United States Patent
Kitahara

(10) Patent No.: US 10,426,437 B2
(45) Date of Patent: Oct. 1, 2019

(54) MEDICAL INPUT DEVICE

(71) Applicant: OLYMPUS CORPORATION, Tokyo (JP)

(72) Inventor: Toshihiro Kitahara, Tachikawa (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/846,465

(22) Filed: Dec. 19, 2017

(65) Prior Publication Data

US 2018/0103929 A1   Apr. 19, 2018

Related U.S. Application Data

(63) Continuation of application No. PCT/JP2016/060835, filed on Mar. 31, 2016.

(30) Foreign Application Priority Data

Jun. 30, 2015   (JP) ................... 2015-130984

(51) Int. Cl.
  *A61B 8/00*   (2006.01)
  *G06F 3/0354*   (2013.01)
  (Continued)

(52) U.S. Cl.
  CPC ............... *A61B 8/467* (2013.01); *A61B 8/00* (2013.01); *A61B 8/12* (2013.01); *B08B 1/002* (2013.01); *G06F 3/016* (2013.01); *G06F 3/0312* (2013.01); *G06F 3/0317* (2013.01); *G06F 3/0354* (2013.01); *G06F 3/03549* (2013.01)

(58) Field of Classification Search
  CPC ... G06F 3/0312; G06F 3/0354; G06F 3/03549
  See application file for complete search history.

(56) References Cited

U.S. PATENT DOCUMENTS 6,144,370 A * 11/2000 Eleyan ............... G06F 3/03549
                                                   273/148 B
2004/0036677 A1  2/2004 Ono et al.
2007/0146328 A1  6/2007 Li

FOREIGN PATENT DOCUMENTS

JP  2002189562 A  7/2002
JP  2004265017 A  9/2004
(Continued)

OTHER PUBLICATIONS

International Search Report dated Apr. 26, 2016 issued in PCT/JP2016/060835.
(Continued)

*Primary Examiner* — Roy P Rabindranath
(74) *Attorney, Agent, or Firm* — Scully Scott Murphy & Presser, P.C.

(57) ABSTRACT

A medical input device for receiving an input of a command signal is provided. The medical input device includes: a main body unit that is a housing; a track ball housed in the main body unit and provided rotatably; an opening forming member configured to form at least an opening having a diameter smaller than that of the track ball, the track ball partially protruding through the opening; and a moving member having an inclined surface on which the track ball is configured to ride, the moving member being movable in a direction of approaching the track ball or in a direction of receding from the track ball.

14 Claims, 11 Drawing Sheets

(51) Int. Cl.
*A61B 8/12* (2006.01)
*B08B 1/00* (2006.01)
*G06F 3/03* (2006.01)
*G06F 3/01* (2006.01)

(56) References Cited

FOREIGN PATENT DOCUMENTS

| | | |
|---|---|---|
| JP | 2010165033 A | 7/2010 |
| JP | 2011210113 A | 10/2011 |
| WO | 02/075641 A1 | 9/2002 |

OTHER PUBLICATIONS

Extended Supplementary European Search Report dated Feb. 1, 2019 in European Patent Application No. 16 81 7528.9.

* cited by examiner (a)　　　　　　　　　　　　(b)

MEDICAL INPUT DEVICE

CROSS REFERENCES TO RELATED APPLICATIONS

This application is a continuation of PCT international application Ser. No. PCT/JP2016/060835, filed on Mar. 31, 2016 which designates the United States, incorporated herein by reference, and which claims the benefit of priority from Japanese Patent Application No. 2015-130984, filed on Jun. 30, 2015, incorporated herein by reference.

BACKGROUND

1. Technical Field

The disclosure relates to a medical input device.

2. Related Art

In order to examine or observe characteristics of body tissues or material as an observation target, an image generated by imaging or an image generated by ultrasound may sometimes be applied. The diagnosis of the body tissues inside the body uses an ultrasound endoscope including an ultrasound transducer and an image sensor at a distal end of an insertion unit.

In the diagnosis by the ultrasound endoscope, for example, an image generated by an image processing apparatus on the basis of the ultrasound echo or an imaging signal obtained by the ultrasound endoscope is displayed on a monitor. Settings of an examination mode and observation conditions at the time of diagnosis, or the like, are performed on the basis of a command signal input via an input device.

A technique employing a spherical track ball is known as an exemplary input device, (refer to, for example, JP 2011-210113 A). JP 2011-210113 A discloses a track ball device in which a track ball is held by first and second casings that are removable from each other and constitute a housing. This technique enables an input of a command signal corresponding to the rotation amount and the rotation direction of the track ball, and is known as an input unit having excellent operability.

SUMMARY

In some embodiments, a medical input device for receiving an input of a command signal is provided. The medical input device includes: a main body unit that is a housing; a track ball housed in the main body unit and provided rotatably; an opening forming member configured to form at least an opening having a diameter smaller than that of the track ball, the track ball partially protruding through the opening; and a moving member having an inclined surface on which the track ball is configured to ride, the moving member being movable in a direction of approaching the track ball or in a direction of receding from the track ball.

The above and other features, advantages and technical and industrial significance of this invention will be better understood by reading the following detailed description of presently preferred embodiments of the invention, when considered in connection with the accompanying drawings.

DETAILED DESCRIPTION

Exemplary embodiments of the present invention will be described with reference to the attached drawings. The following description will exemplify an ultrasound diagnosis system including a medical input device that generates an ultrasound image based on an ultrasound echo. The present invention, however, is not limited to these embodiments. The same reference signs are used to designate the same elements throughout the drawings.

First Embodiment

Figure 1:
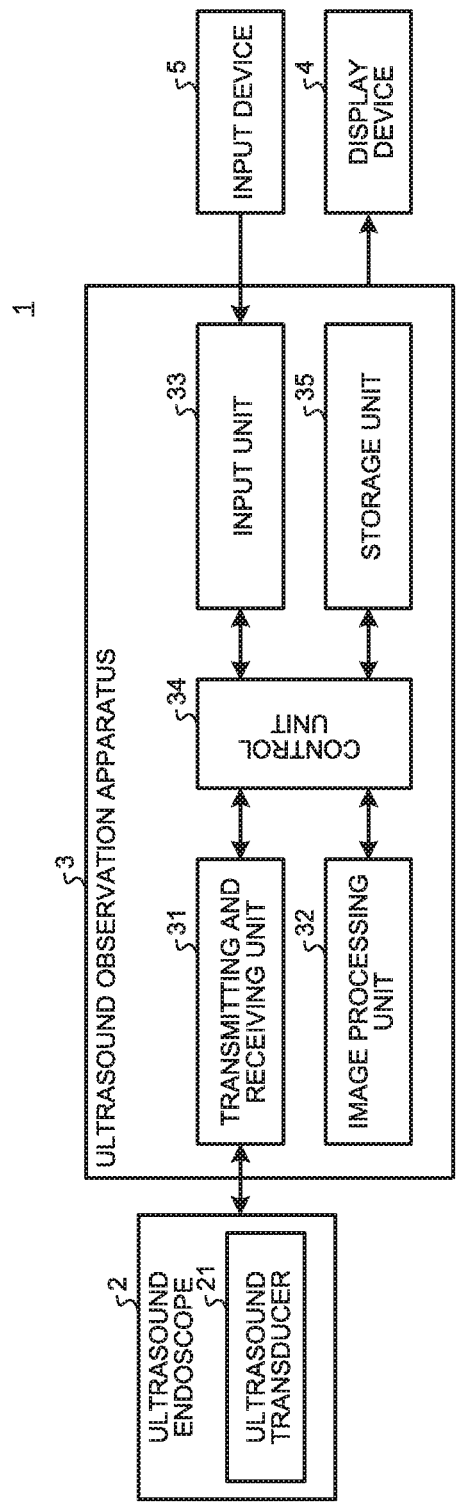
FIG. 1 is a block diagram illustrating a configuration of an ultrasound diagnosis system equipped with an ultrasound observation apparatus according to a first embodiment of the present invention.

FIG. 1 is a block diagram illustrating a functional configuration of an ultrasound diagnosis system equipped with an ultrasound observation apparatus according to a first embodiment of the present invention. An ultrasound diagnosis system 1 illustrated in FIG. 1 includes an ultrasound endoscope 2, an ultrasound observation apparatus 3, a display device 4, and an input device (medical input device) 5. The ultrasound endoscope 2 transmits ultrasound to a subject as an observation target and receives ultrasound reflected on the subject. The ultrasound observation apparatus 3 generates an ultrasound image on the basis of the ultrasound signal obtained by the ultrasound observation apparatus 3. The display device 4 displays the ultrasound image generated by the ultrasound observation apparatus 3. The input device 5 inputs a command signal for examination mode setting, observation condition setting, or the like.

The ultrasound endoscope 2 includes, on its distal end portion, an ultrasound transducer 21. The ultrasound transducer 21 converts an electrical pulse signal received from the ultrasound observation apparatus 3 into an ultrasound pulse (acoustic pulse) and emits it to the subject. The ultrasound transducer 21 also converts an ultrasound echo reflected on the subject into an electrical echo signal (ultrasound signal) expressed by a voltage change and outputs the signal. The ultrasound transducer 21 is realized by a radial transducer. The ultrasound endoscope 2 may cause the ultrasound transducer 21 to perform mechanical scan, or may provide, as the ultrasound transducer 21, a plurality of elements in an array, and may cause the ultrasound transducer to perform electronic scan by electronically switching elements related to transmission/reception or imposing delay onto transmission/reception of each of elements.

The ultrasound endoscope 2 typically includes an imaging unit having an imaging optical system and an image sensor. The ultrasound endoscope 2 can be inserted into gastrointestinal tracts (esophagus, stomach, duodenum, and large intestine) or respiratory organs (trachea, bronchus) of the subject and can capture gastrointestinal tract, respiratory organs, and their surrounding organs (pancreas, gall bladder, bile duct, biliary tract, lymph nodes, mediastinal organs, blood vessels, or the like). The ultrasound endoscope 2 includes a light guide that guides illumination light emitted to the subject at the time of capturing. The light guide is configured such that a distal end portion thereof reaches a distal end of an insertion unit of the ultrasound endoscope 2 into the subject, while a proximal end thereof is connected to a light source device that generates illumination light.

The ultrasound observation apparatus 3 includes a transmitting and receiving unit 31, an image processing unit 32, an input unit 33, control unit 34, and a storage unit 35.

The transmitting and receiving unit 31 performs transmission and reception of electrical signals between the imaging unit and the ultrasound transducer 21. The transmitting and receiving unit 31 is electrically connected with the imaging unit, transmits imaging information such as an imaging timing to the imaging unit and receives an imaging signal generated by the imaging unit. Moreover, the transmitting and receiving unit 31 is electrically connected with the ultrasound transducer 21, transmits an electrical pulse signal to the ultrasound transducer 21, and receives an echo signal as an electrical reception signal from the ultrasound transducer 21. Specifically, the transmitting and receiving unit 31 generates an electrical pulse signal on the basis of a preset waveform and transmission timing and transmits the generated pulse signal to the ultrasound transducer 21.

The transmitting and receiving unit 31 performs sensitivity time control (STC) correction that amplifies an echo signal having a larger receiving depth by using a higher amplification factor. The transmitting and receiving unit 31 performs processing such as filtering on the amplified echo signal, and thereafter, generates digital high-frequency signal, namely, a radio frequency (RF) signal of time domain by performing A/D conversion on the signal, and outputs the generated signal.

The image processing unit 32 generates endoscopic image data based on the imaging signal and generates image data corresponding to the electrical echo signal.

The input unit 33 receives the command signal input by the input device 5 and receives an input of various types of information corresponding to the received command signal. Examples of the various types of information include examination mode setting and observation condition setting (for example, switching of gain and display range, and scroll instruction information (sliding direction and sliding amount of B mode image)).

The control unit 34 controls the entire ultrasound diagnosis system 1. The control unit 34 includes a CPU having calculation/control functions, various calculation circuits, or the like. The control unit 34 reads, from the storage unit 35, information stored in the storage unit 35, and executes various types of calculation processing related to the method for operating the ultrasound observation apparatus 3, thereby integrally controlling the ultrasound observation apparatus 3. The control unit 34 and the image processing unit 32 may share the same CPU.

The storage unit 35 stores various programs for operating the ultrasound diagnosis system 1, data including various parameters needed for operation of the ultrasound diagnosis system 1, or the like. The storage unit 35 stores, for example, an initial position (sound ray number) of a writing position (ultrasound transmission start position) of the ultrasound image.

The storage unit 35 also stores various programs including an operation program for executing a method for operating the ultrasound diagnosis system 1. The operation programs can be recorded in a computer-readable recording medium such as a hard disk, flash memory, CD-ROM, DVD-ROM, flexible disk, or the like, and can be distributed broadly. It is also possible to obtain the above-described various programs by downloading them via a communication network. Herein, the communication network refers to one implemented by, for example, a known public network, a local area network (LAN), a wide area network (WAN), regardless of wired or wireless.

The above-configured storage unit 35 is formed with a read only memory (ROM) in which various programs are pre-installed, a random access memory (RAM) that stores calculation parameters and data for each of processing, or the like.

Figure 2:
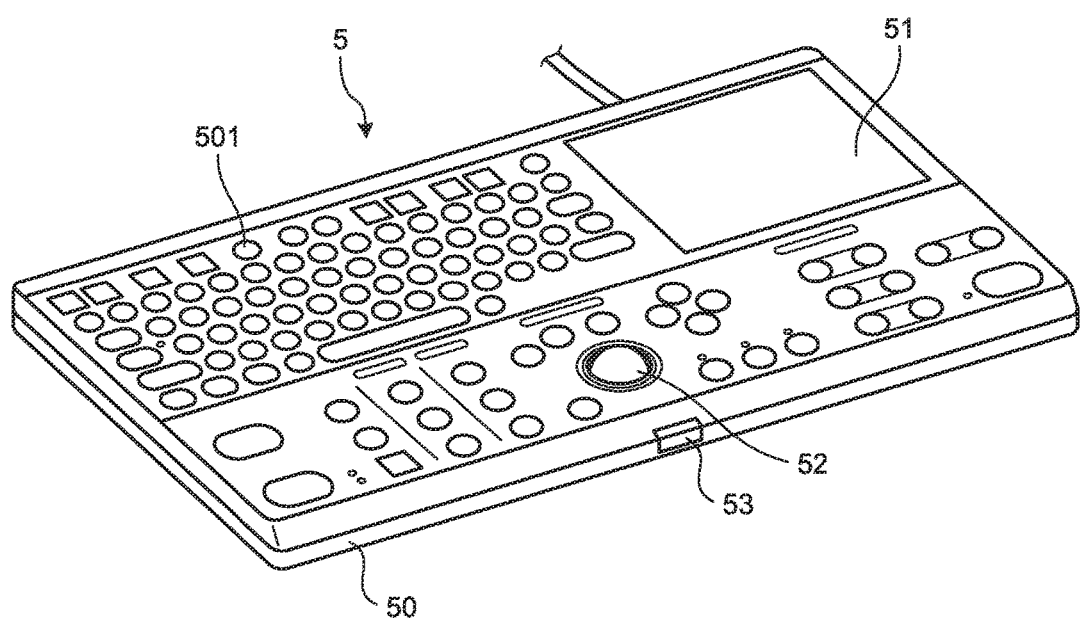
FIG. 2 is a perspective view illustrating a configuration of an input device according to the first embodiment of the present invention.

Next, the input device 5 will be described with reference to FIGS. 2 to 9. FIG. 2 is a perspective view illustrating the configuration of the input device according to the first embodiment.

As illustrated in FIG. 2, the input device 5 includes a main body unit 50 as a housing, a display unit 51, a track ball 52, and a press button 53. The display unit 51 is provided on one surface of the main body unit 50 and capable of displaying various types of information. The track ball 52 has a spherical shape and is provided in a state where the track ball 52 is partially exposed from the surface of the main body unit 50. The press button 53 is pressed when the track ball 52 is extracted from the main body unit 50. Moreover, a plurality of keys 501 arranged on the input device 5 is exposed from the main body unit 50 and can be depressed. The input device 5 is electrically connected to the ultrasound observation apparatus 3 via a cable and inputs information on the rotation amount and rotation direction of the track ball and a command signal by depressing the key 501, to the input unit 33.

On the input device 5, when the track ball 52 is rotated by operation of an operator, for example, an optical sensor (not illustrated) detects the rotation amount and the rotation direction of the track ball 52, generates information indicating a detection result, and outputs the information to the ultrasound observation apparatus 3. The ultrasound observation apparatus 3 performs signal processing corresponding to the input rotation amount and rotation direction, on the basis of the received information.

Figure 3:
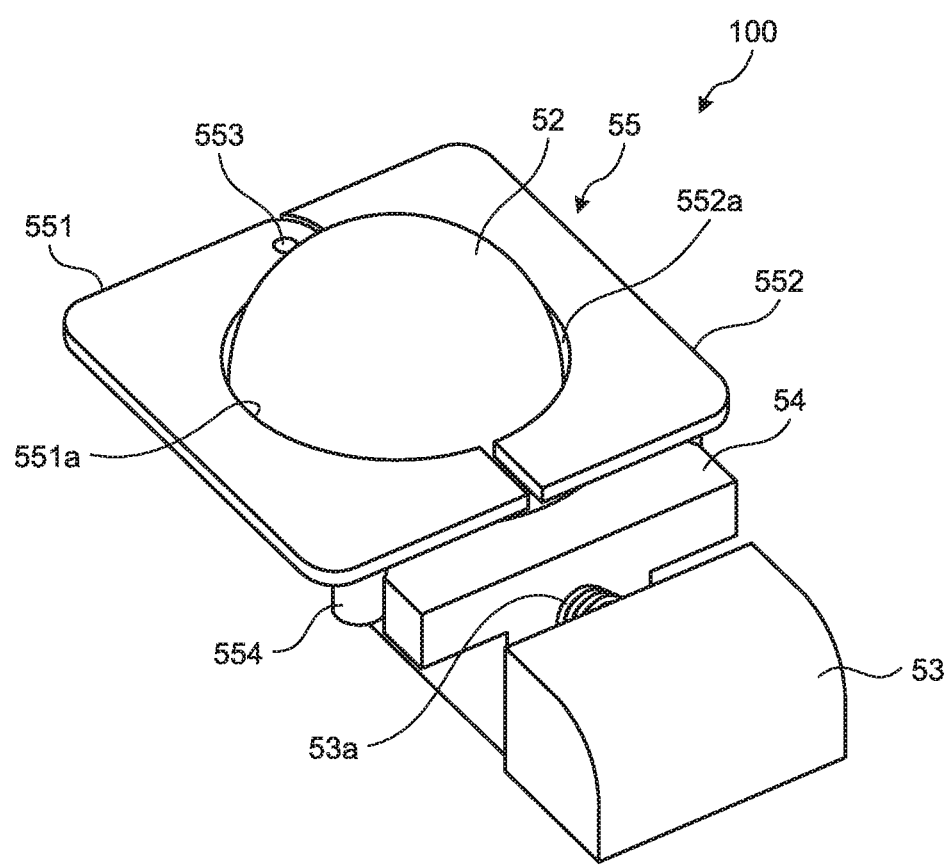
FIG. 3 is a perspective view illustrating a configuration of main parts of the input device according to the first embodiment of the present invention.
Figure 4:
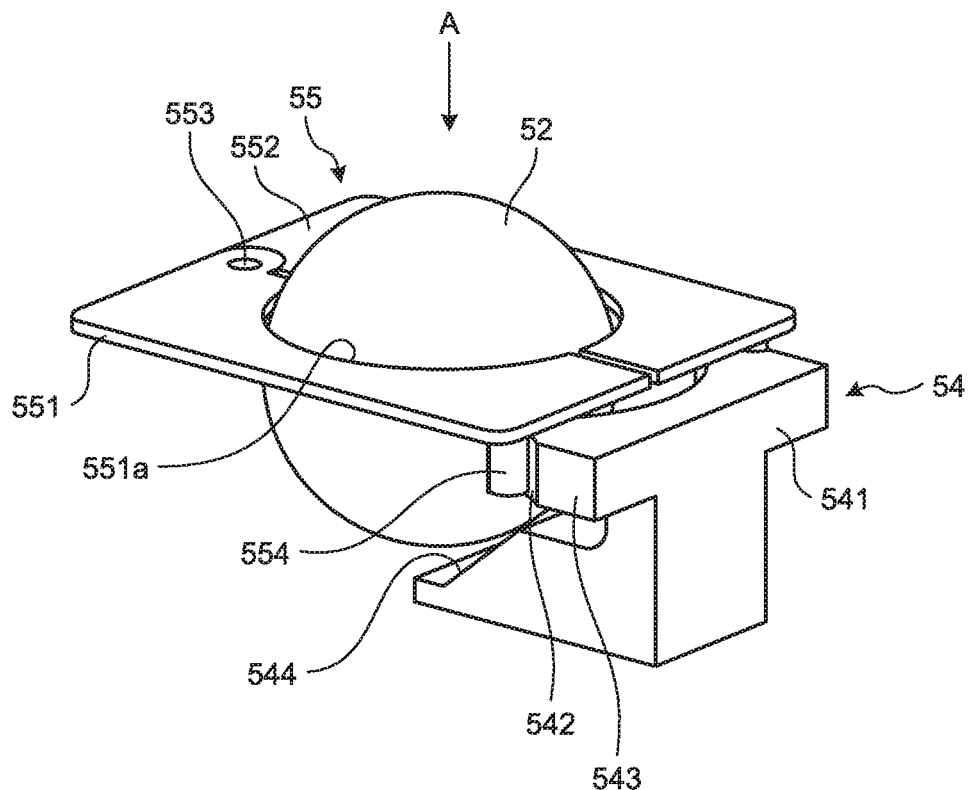
FIG. 4 is a perspective view illustrating a configuration of the main parts of the input device according to the first embodiment of the present invention.
Figure 5:
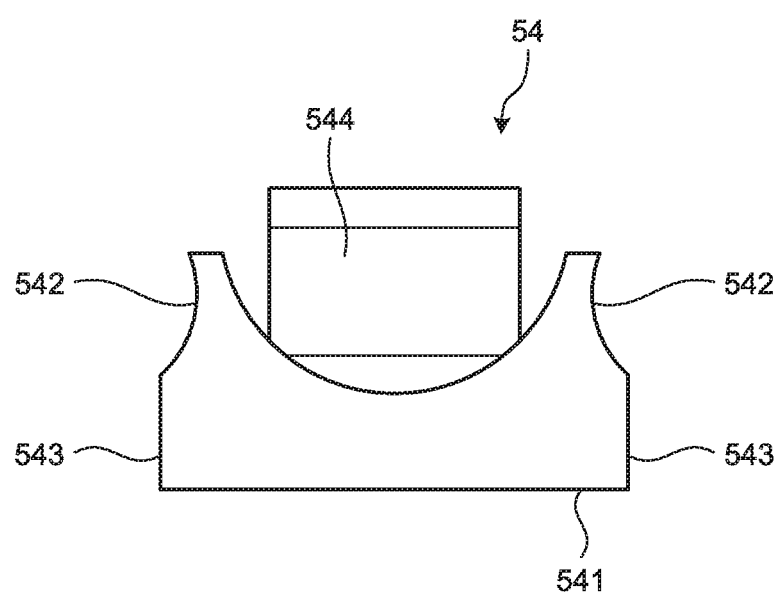
FIG. 5 is a plan view illustrating a configuration of the main parts of the input device according to the first embodiment of the present invention.
Figure 6:
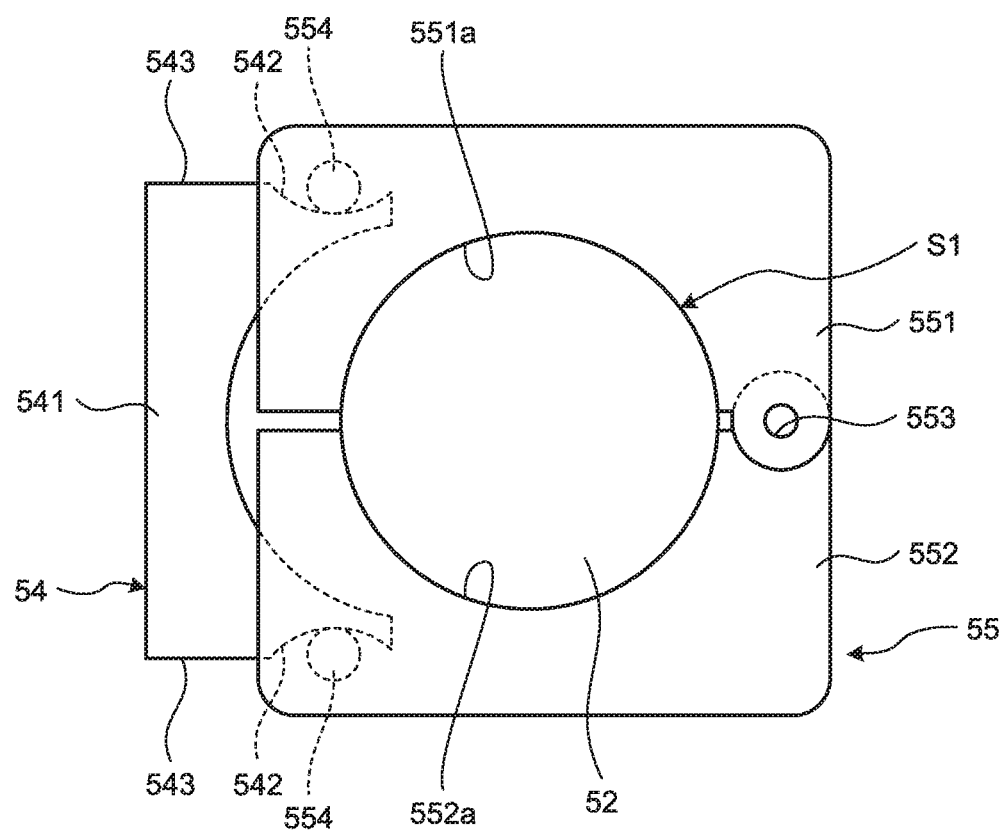
FIG. 6 is a plan view illustrating a configuration of the main parts of the input device according to the first embodiment of the present invention.

Subsequently, a configuration and a method for extracting the track ball 52 from the main body unit 50 will be described with reference to FIGS. 3 to 9. FIG. 3 is a perspective view illustrating a configuration of main parts of the input device according to the first embodiment, illustrating the track ball 52 and an extraction mechanism for extracting the track ball 52. FIG. 4 is a perspective view illustrating a configuration of the main parts of the input device according to the first embodiment, in which the press button 53 is removed from the configuration illustrated in FIG. 3. FIG. 5 is a plan view illustrating a configuration of the main parts of the input device according to the first embodiment, illustrating the configuration of a moving member 54. FIG. 6 is a plan view illustrating a configuration of the main parts of the input device according to the first embodiment, illustrating the configuration in the direction of arrow A illustrated in FIG. 4.

An extraction mechanism 100 for extracting the track ball 52 from the main body unit 50 is provided inside the main body unit 50. As illustrated in FIG. 3, the extraction mechanism 100 includes the above-described press button 53, the moving member 54, and an opening forming member 55. The moving member 54 is connected to the press button 53 and movable in a direction of approaching the track ball 52 or in a direction of receding from the track ball 52. When the press button 53 is pressed, the moving member 54 moves toward the track ball 52 in accordance with the load by the pressing. The opening forming member 55 is capable of forming an opening having a diameter that locks the track ball 52 or an opening having a diameter that allows passing of the track ball 52. The size of the diameter of the opening forming member 55 changes in conjunction with the movement of the moving member 54.

The moving member 54 includes a base 541, two arms 542, a side surface portion 543, and an inclined portion 544. The base 541 receives a load from the press button 53 and is movable in a direction of moving toward the track ball 52 in accordance with the received load. The two arms 542 extend from the base 541. The side surface portion 543 constitutes a portion of a side surface of the base 541 and is continuous with the arm 542. The inclined portion 544 is provided on a side that is opposite to a side to which load is applied from the press button 53 of the base 541 and that faces the track ball 52. The inclined portion 544 has an inclined surface inclined in a moving direction of the base 541. The distance between the outer surfaces of the opposing arms 542 is smaller than the distance between the outer surfaces of the opposing side surface portions 543. The term "outer surface" as used herein refers to the surface opposite to the mutually opposing sides. Moreover, the inclined surface of the inclined portion 544 also includes a step-like surface whose height changes stepwise.

The opening forming member 55 includes a first opening forming member 551 and a second opening forming member 552, capable of respectively forming a large diameter opening or a small diameter opening with respect to the track ball 52 diameter. Each of the first opening forming member 551 and the second opening forming member 552 is pivotably supported on a rotation shaft 553 fixed inside the main body unit 50. Moreover, each of the first opening forming member 551 and the second opening forming member 552 is in contact with, for example, each of end portions of torsion springs (not illustrated) provided on the rotation shaft 553, and thus, is in a state where a load is applied in a direction of allowing the end on the rotation shaft 553 side and the end on the side opposite to the rotation shaft 553 side to move toward each other.

Moreover, each of the first opening forming member 551 and the second opening forming member 552 includes an abutment pin 554 that respectively abuts each of the arms 542 and the side surface portion 543 continuous with the each of the arms 542. In the first embodiment, the arm 542, the side surface portion 543 and the abutment pin 554 constitute a diameter expanding unit.

The first opening forming member 551 is formed on the side opposing the second opening forming member 552 and includes a first opening forming portion 551a in an arc shape. The second opening forming member 552 is formed on the side opposing the first opening forming member 551 and includes a second opening forming portion 552a in an arc shape. An opening S1 (refer to FIG. 6) is formed by the first opening forming portion 551a and the second opening forming portion 552a. In a case where the opening S1 forms a circle, the diameter of this circle is smaller than the diameter of the track ball 52. When the opening S1 has an elliptical shape or a shape other than a circle, the minimum length among the lengths of the openings passing through the center is smaller than the diameter of the track ball 52.

Moreover, a damper mechanism is provided between the press button 53 and the moving member 54. Specifically, a coil spring 53a is provided between the press button 53 and the moving member 54, whereby the load at the time when the press button 53 is pressed is reduced to suppress the moving speed of the moving member 54, while the press button 53 is returned to a normal position in a case where the pressing of the press button 53 is released. Here, the normal position is the position of the press button 53 before being pressed. It is not necessary to provide the damper mechanism.

Figure 7:
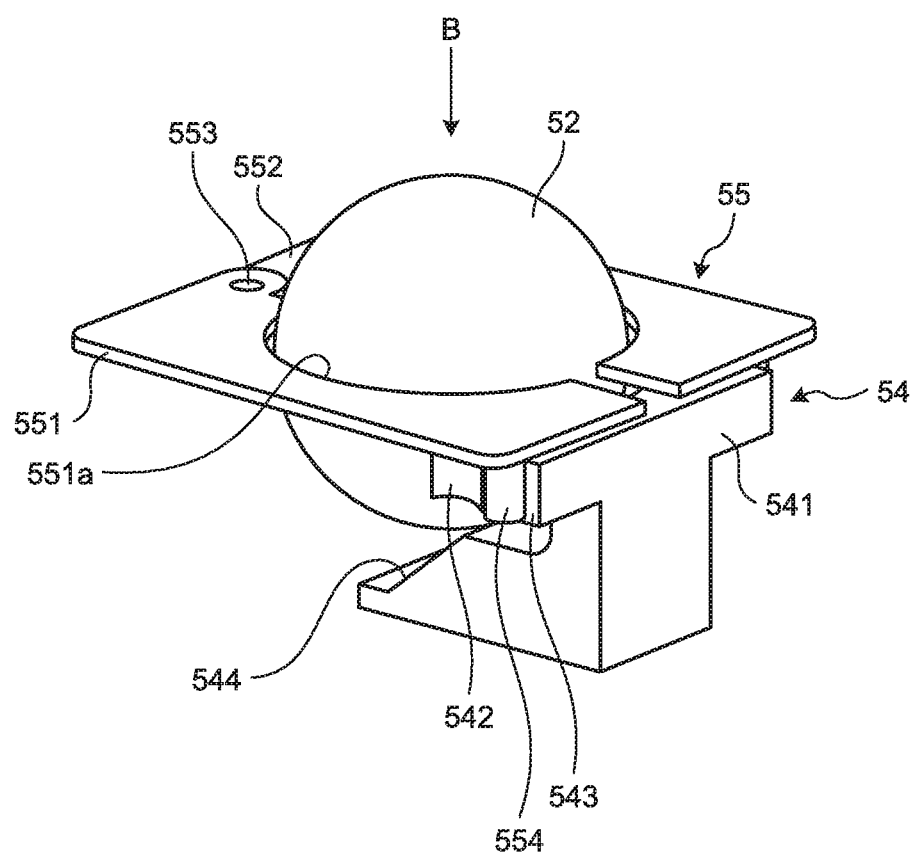
FIG. 7 is a perspective view illustrating a configuration of the main parts of the input device according to the first embodiment of the present invention.
Figure 8:
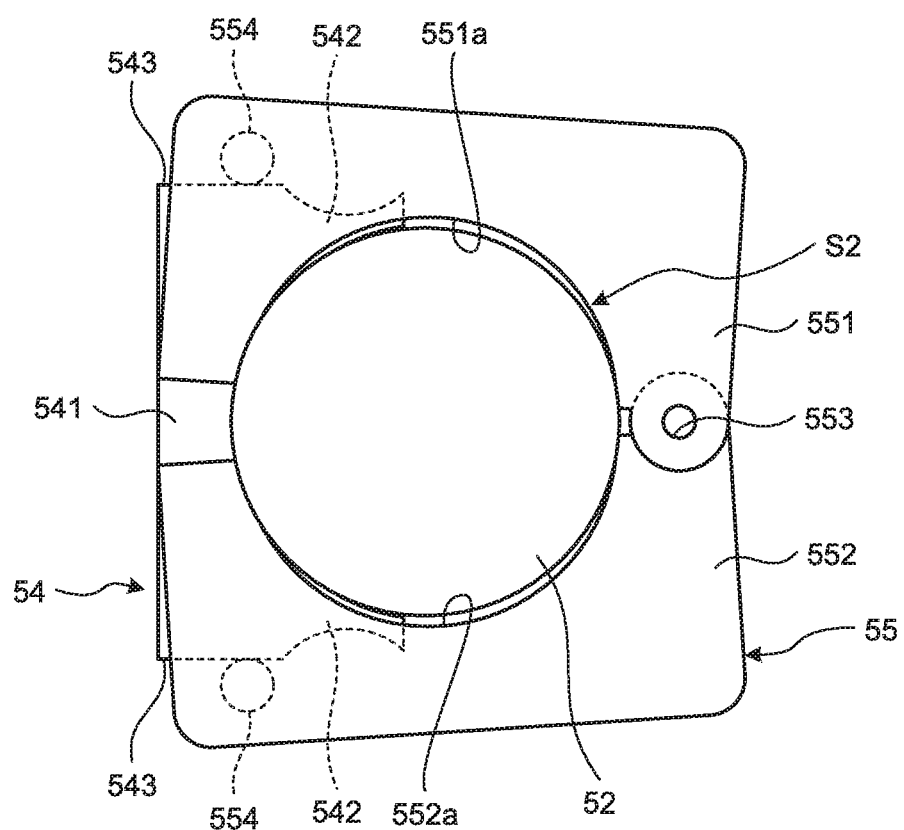
FIG. 8 is a plan view illustrating a configuration of the main parts of the input device according to the first embodiment of the present invention.

FIG. 7 is a perspective view illustrating a configuration of the main parts of the input device according to the first embodiment, illustrating a case where the press button 53 is pressed. FIG. 8 is a plan view illustrating a configuration of the main parts of the input device according to the first embodiment, illustrating a configuration in the direction of arrow B illustrated in FIG. 7.

When the press button 53 is pressed and the moving member 54 moves toward the track ball 52, the abutment pin 554 moves along the outer surface of the arm 542 in conjunction with the movement of the moving member 54. When the abutment pin 554 moves from the arm 542 to the side surface portion 543 along the movement of the moving member 54 as illustrated in FIGS. 7 and 8, the first opening forming member 551 and the second opening forming member 552 rotate around the rotation shaft 553 in conjunction with the movement.

When the first opening forming member 551 and the second opening forming member 552 rotate around the rotation shaft 553, the end portions of the first opening forming member 551 and the second opening forming member 552, which are on the opposite side of the rotation shaft 553, move away from each other. Accordingly, the diameter of an opening S2 formed by the first opening forming portion 551a and the second opening forming portion 552a, for example, the diameter of the circle inscribed in the opening S2, becomes larger than the diameter of the opening S1. It is preferable that the diameter of the expanded opening S2 is larger than the diameter of the track ball 52. The diameter of the opening S2 may be not larger than the diameter of the track ball 52 provided that a coating, or the like, that can suppress damage on the track ball 52 is applied to portions that come in contact with the track ball 52, on each of the first opening forming portion 551a and the second opening forming portion 552a.

When the press button 53 is pressed and the moving member 54 moves toward the track ball 52, the track ball 52 rides on the inclined surface of the inclined portion 544 in conjunction with the movement of the moving member 54. The track ball 52 moves upward with respect to the moving member 54, that is, the amount of protrusion of the track ball 52 from the surface of the main body unit 50 increases, in accordance with the entering amount of the inclined portion 544.

At the time of changing from the opening S1 to the opening S2 and at the time of lifting the track ball 52 by the inclined portion 544, it is preferable not to contact the track ball 52 with the first opening forming portion 551a and the second opening forming portion 552a. The time of changing from the opening S1 to the opening S2 and the time of lifting the track ball 52 are adjustable by the arrangement of the arm 542, the side surface portion 543, and the inclined surface of the inclined portion 544 and an angle of the inclined surface of the inclined portion 544.

Figure 9:
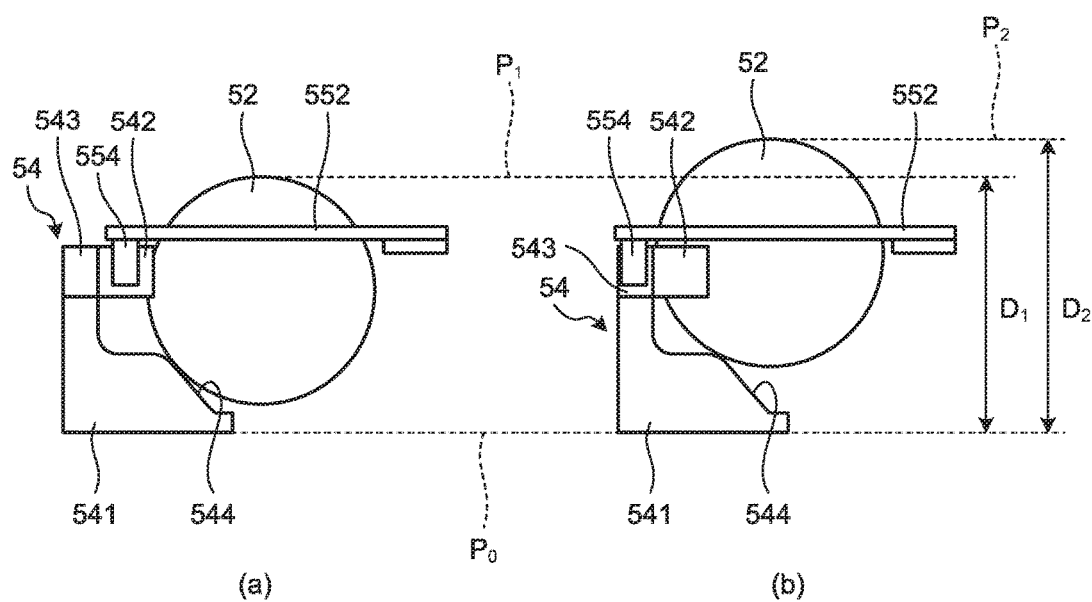
FIG. 9 is a view illustrating extraction of a track ball in the input device according to the first embodiment of the present invention.

FIG. 9 is a diagram illustrating extraction of the track ball in the input device according to the first embodiment. Specifically, (a) of FIG. 9 illustrates a state before the press button 53 is pressed, and (b) of FIG. 9 illustrates a state after the press button 53 is pressed. As illustrated in FIG. 9, when a surface passing through a bottom of the moving member 54 is represented by $P_0$, a surface that is in parallel with the surface $P_0$ and is in contact with a distal end of the track ball 52 before pressing is represented by $P_1$, and a surface that comes in contact with the distal end of the pressed track ball 52 is represented by $P_2$, a distance $D_2$ between the surface $P_0$ and the surface $P_2$ is greater than a distance $D_1$ between the surface $P_0$ and the surface $P_1$.

In this manner, after the press button 53 is pressed, the diameter of the opening S2 increases so as not to contact with the track ball 52, which leads to an increase in the amount of protrusion of the track ball 52 from the surface of the main body unit 50. This makes it possible to easily extract the track ball 52 by merely pressing the press button 53. The amount of protrusion of the track ball 52 from the main body unit 50 can be easily adjusted by changing the angle of the inclined surface of the inclined portion 544.

Moreover, when the track ball 52 is attached onto the main body unit 50, the press button 53 is depressed to expand the opening formed by the first opening forming portion 551a and the second opening forming portion 552a (to form the opening S2), and then, the track ball 52 is dropped into the main body unit 50 from the opening S2. Thereafter, when the pressed state of the press button 53 is released, the inclined portion 544 retreats from the track ball 52 by the self-weight of the track ball 52 or a biasing member such as a coil spring (not illustrated), while the diameter of the opening formed by the first opening forming portion 551a and the second opening forming portion 552a returns to the diameter of the opening S1, and the moving member 54 returns to the normal position.

A latch mechanism may be provided such that the position of the moving member 54 is held by the latch mechanism. For example, when the pressing amount of the press button 53 (moving amount of the moving member 54) reaches a predetermined amount, the latch mechanism is turned on (holding state), and when the press button 53 is further pressed, the latching mechanism is turned off (holding release state). At this time, the object to be held by the latch mechanism may be the moving member 54 or the press button 53.

In the first embodiment described above, the opening S1 formed by the first opening forming portion 551a and the second opening forming portion 552a is smaller than the track ball 52 in diameter when the press button 53 is not pressed, making it possible to prevent the track ball 52 from falling from the main body unit 50. In contrast, by pressing the press button 53, the diameter of the opening formed by the first opening forming portion 551a and the second opening forming portion 552a is changed to the opening S2 so as not to contact with the track ball 52, and the track ball 52 rides on the inclined portion 544, which leads to the increased amount of protrusion of the track ball 52 from the surface of the main body unit 50. In this manner, according to the first embodiment, it is possible to easily attach and detach the track ball 52 to and from the main body unit 50 merely by depressing the press button 53.

First Modification of First Embodiment

Figure 10:
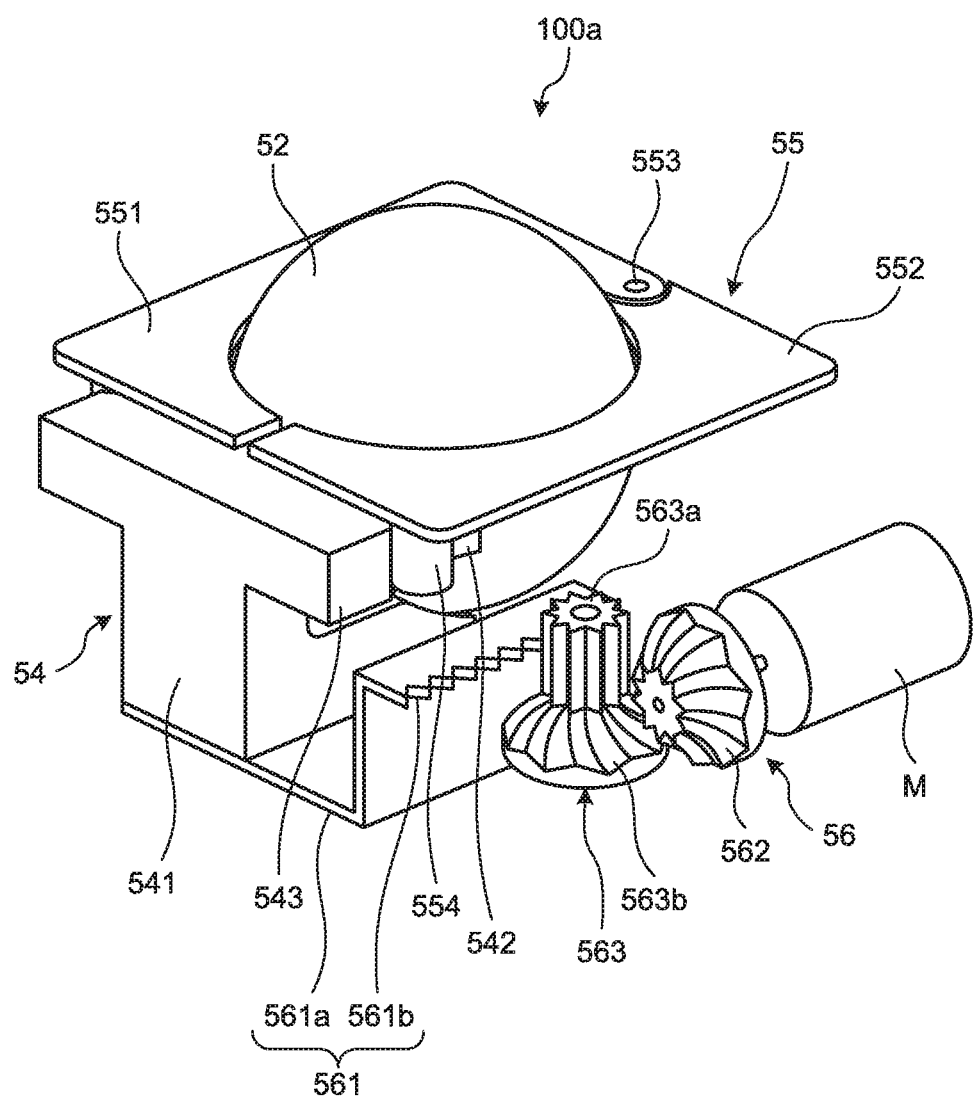
FIG. 10 is a perspective view illustrating a configuration of main parts of an input device according to a first modification of the first embodiment of the present invention.

Next, a first modification of the first embodiments of the present invention will be described. FIG. 10 is a perspective view illustrating a configuration of main parts of an input device according to the first modification of the first embodiment of the present invention, illustrating the track ball 52 and an extraction mechanism for extracting the track ball 52. The same reference signs are used to designate the same elements as those in the first embodiment. While the press button 53 is provided in the first embodiment, the moving member 54 is configured to be moved under the control of a motor M (driving source) without providing the press button 53 in the first modification.

An extraction mechanism 100a illustrated in FIG. 10 includes the above-described moving member 54, the opening forming member 55, and a drive unit 56 configured to transmit a driving force generated by the motor M to move the moving member 54 in a direction of approaching the track ball 52 or in a direction of receding from the track ball 52.

The drive unit 56 includes a supporting-moving unit 561, a first gear 562, and a second gear 563. The supporting-moving unit 561 supports the moving member 54 and is movable in a direction of approaching the track ball 52 or in a direction of receding from the track ball 52. The first gear 562 is connected to the motor M that generates motive power regarding the movement of the supporting-moving unit 561 and is rotatable by rotation of the motor M. The second gear 563 is provided between the supporting-moving unit 561 and the first gear 562.

The supporting-moving unit 561 includes a supporting section 561a and a first meshing section 561b. The supporting section 561a supports the moving member 54. The first meshing section 561b is continuous with the supporting section 561a and has a saw-tooth pattern extending in a direction of moving the supporting-moving unit 561 to mesh with the second gear 563. The second gear 563 coaxially includes a second meshing section 563a and a third meshing section 563b. The second meshing section 563a is configured to mesh with the first meshing section 561b. The third meshing section 563b is configured to mesh with the first gear 562.

In the first modification, the rotation of the motor M causes the second gear 563 to rotate, thereby causing the third meshing section 563b to rotate in conjunction with the rotation of the second gear 563. The rotation of the third meshing section 563b causes the second meshing section 563a to rotate, thereby causing the supporting-moving unit 561 to move via the first meshing section 561b. The movement of the supporting-moving unit 561 enables the moving member 54 to move in a direction of approaching the track ball 52 or in a direction of receding from the track ball 52.

According to the first modification, it is possible to obtain the same effects as in the first embodiment as well as to easily extract the track ball 52 merely by controlling the motor M. In the first embodiment, the track ball 52 is extracted while the user keeps pressing the press button 53. Alternatively, the first modification enables controlling the rotation of the motor M on the basis of the depression of a key 501, or the like. This configuration enables, for example, the track ball 52 to move forward and backward from the main body unit 50 by merely depressing the key 501 once, making it possible to extract or attach the track ball 52 more easily.

Moreover, the first modification may be configured such that the motor M is driven on the basis of a control signal from the ultrasound observation apparatus 3.

The moving member 54 may be moved by driving the motor M under the control of the input device 5 or the ultrasound observation apparatus 3 when a predetermined condition is satisfied. For example, if the number of times of startup of the apparatus is adopted as the predetermined condition and when a predetermined number of times of power supply startup is reached, the motor M is driven to automatically move the track ball 52 to an extraction position at the time of power supply startup and to urge the user to clean the track ball 52. In this case, for example, the ultrasound observation apparatus 3 counts the number of times of power supply startup (apparatus startup by power supply from the ultrasound observation apparatus 3), and then, in a case where the count has reached the predetermined number, the motor M is driven to move the track ball 52 to the extraction position. The motor M may be controlled on the input device 5 side.

While the driving force of the motor M is transmitted by meshing in the first modification, it is also possible to use a known power transmission means such as transmission of rotational power by a frictional force or transmission of rotational power using a belt, or the like.

Second Modification of First Embodiment

Figure 11:
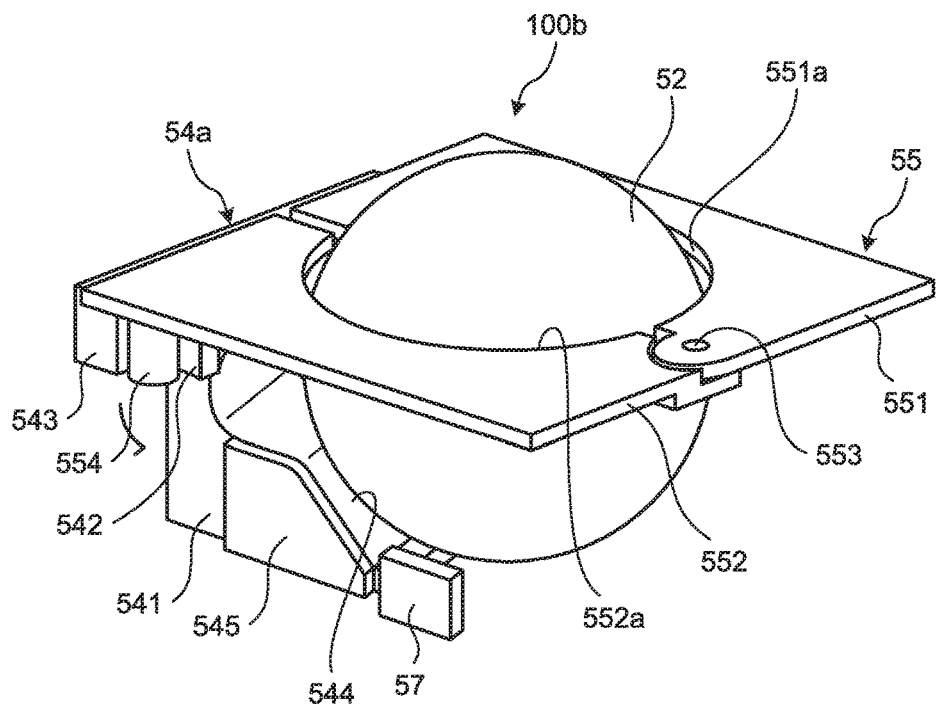
FIG. 11 is a perspective view illustrating a configuration of main parts of an input device according to a second modification of the first embodiment of the present invention.
Figure 12:
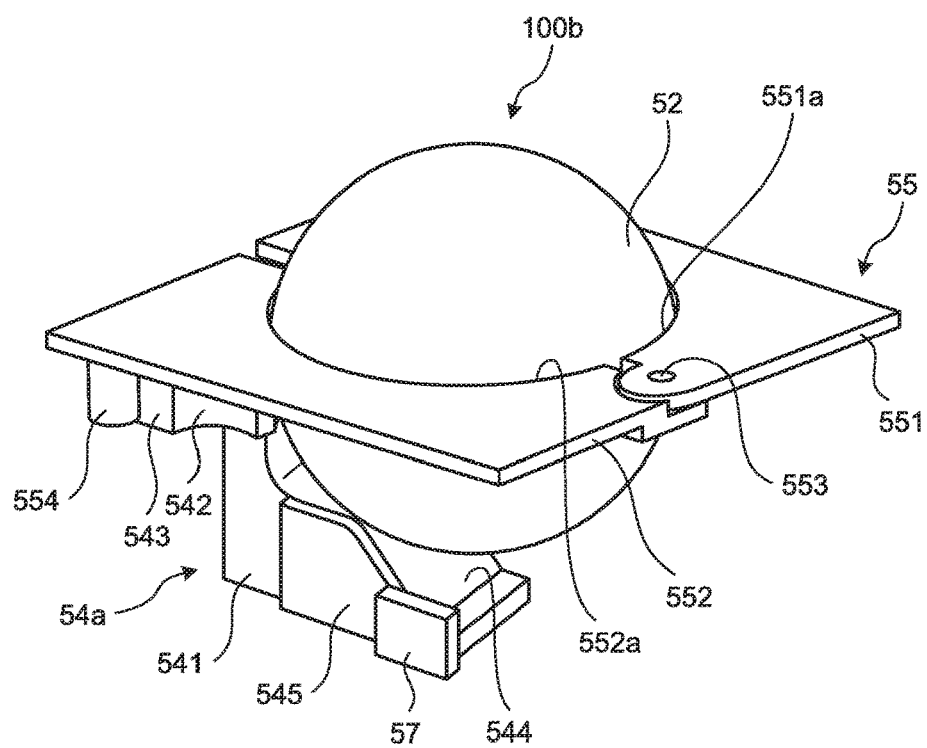
FIG. 12 is a perspective view illustrating a configuration of the main parts of the input device according to the second modification of the first embodiment of the present invention.

Next, a second modification of the first embodiment of the present invention will be described. FIGS. 11 and 12 are perspective views illustrating a configuration of main parts of an input device according to the second modification of the first embodiment of the present invention, illustrating the track ball 52 and an extraction mechanism 100b for extracting the track ball 52. The same reference signs are used to designate the same elements as those in the first embodiment. In addition to the configuration according to the above-described first embodiment, the configuration of the second modification includes a cleaning unit 545 that cleans a detection sensor 57 configured to detect the rotation amount and the rotation direction of the track ball 52. In the second modification, the track ball 52 has a patterned or irregular surface, and information (rotation amount and rotation direction) related to the rotation of the track ball 52 is detectable by the optical detection sensor 57. Specifically, the detection sensor 57 is fixed to the main body unit 50, emits light to a predetermined position of the track ball, receives reflected light, and outputs the received light to a calculation unit, or the like, in the main body unit 50 as detection information (track ball 52 movement information). The detection sensor 57 may be a sensor for receiving light emitted from the outside and reflected from the track ball 52, that is, a sensor for receiving light only.

The moving member 54a includes the cleaning unit 545 on a side surface of the inclined portion 544, orthogonal to the inclined surface and facing the detection sensor 57. The cleaning unit 545 is in sliding contact with a light emitting/receiving surface of the detection sensor 57, and removes extraneous matter from the light emitting/receiving surface. The cleaning unit 545 is provided so as to be in sliding contact with the light emitting/receiving surface of the detection sensor 57 during the movement of the moving member 54a toward the track ball 52 side at the time of removal of the track ball 52 (refer to FIG. 12). Moreover, the cleaning unit 545 has a surface formed of cloth or elastically deformable material with concavo-convex patterns, for example, the surface being configured to be in contact with the light emitting/receiving surface. The cleaning unit 545 may be formed by a brush-like member.

According to the second modification, it is possible to obtain the same effect as in the first embodiment. In addition, the cleaning unit 545 is in sliding contact with the light emitting/receiving surface of the detection sensor 57 to perform cleaning while the moving member 54a is moving toward the track ball 52 at the time of extracting the track ball 52. Accordingly, it is possible to perform cleaning of the detection sensor 57 simultaneously with the extraction of the track ball 52 using the moving member 54a.

Second Embodiment

Figure 13:
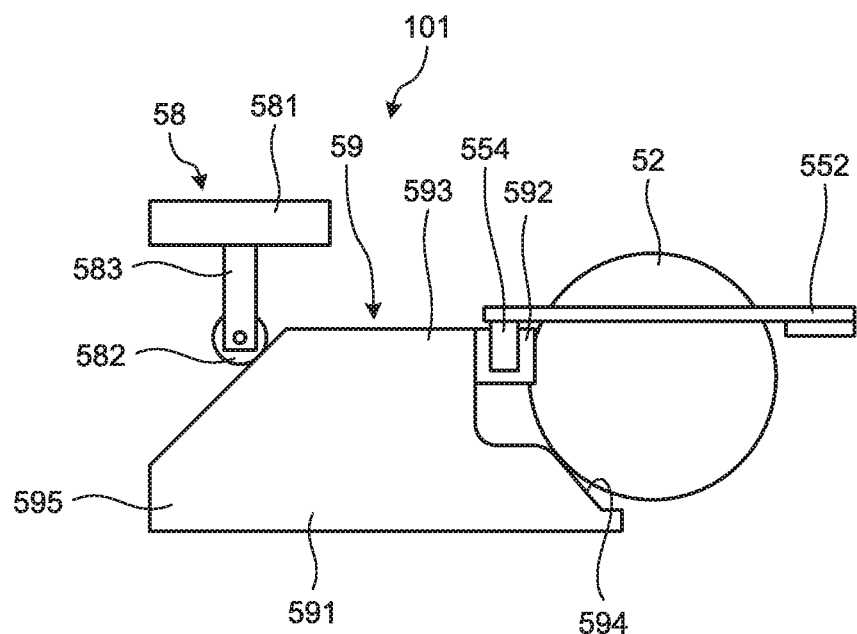
FIG. 13 is a side view illustrating a configuration of main parts of an input device according to a second embodiment of the present invention.

Next, a second embodiment of the present invention will be described. FIG. 13 is a side view illustrating a configuration of main parts of an input device according to the second embodiment, illustrating the track ball 52 and an extraction mechanism for extracting the track ball 52. FIG. 13 is a diagram illustrating a state when the press button is not pressed. The same reference signs are used to designate the same elements as those in the first embodiment. In the above-described first embodiment, the press button is pressed in the direction substantially orthogonal to the extraction direction of the track ball 52. In the second embodiment, however, the press button is pressed in the direction substantially parallel to the extraction direction of the track ball 52.

The input device according to the second embodiment includes the main body unit 50, the display unit 51, the track ball 52, and a press button 58 that is pressed when the track ball 52 is extracted from the main body unit 50. Moreover, an extraction mechanism 101 for extracting the track ball 52 from the main body unit 50 is provided inside the main body unit 50.

Subsequently, a configuration and a method for extracting the track ball 52 from the main body unit 50 will be described. The extraction mechanism 101 for extracting the track ball 52 from the main body unit 50 includes the above-described press button 58, a moving member 59, and the opening forming member 55. The moving member 59 comes in contact with the press button 58, and moves in a direction of moving toward the track ball 52 in accordance with the load by the pressing when the press button 58 is pressed. The opening forming member 55 is capable of forming an opening having a diameter that locks the track ball 52, or an opening having a diameter that allows passing of the track ball 52. The size of the diameter of the opening of the opening forming member 55 changes in conjunction with the movement of the moving member 59.

The press button 58 includes a press section 581, a roller 582, and a holding section 583. The press section 581 is pressed by the user. The roller 582 comes in contact with the moving member 59. The holding section 583 extends in a direction substantially parallel to the direction to which a load by pressing is applied from the press section 581, and rotatably holds, at its distal end, the roller 582.

The moving member 59 includes a base 591, two arms 592, a side surface portion 593, an inclined portion 594, and an abutment portion 595. The base 591 receives a load from the press button 58 (roller 582) and is movable in a direction of moving toward the track ball 52 in accordance with the received load. The two arms 592 extend from the base 591 (although solely one of the two is illustrated in FIG. 13). The side surface portion 593 constitutes a portion of a side surface of the base 591 and is continuous with the arm 592. The inclined portion 594 is provided on a side that is opposite to a side to which load is applied from the press button 58 of the base 591 and that faces the track ball 52. The inclined portion 594 has an inclined surface inclined in a moving direction of the base 591. The abutment portion 595 is continuous with the base 591 and includes an inclined surface that abuts the roller 582. Similarly to the above-described first embodiment, the distance between the outer surfaces of the opposing arms 592 is smaller than the distance between the outer surfaces of the opposing side surface portions 593.

Figure 14:
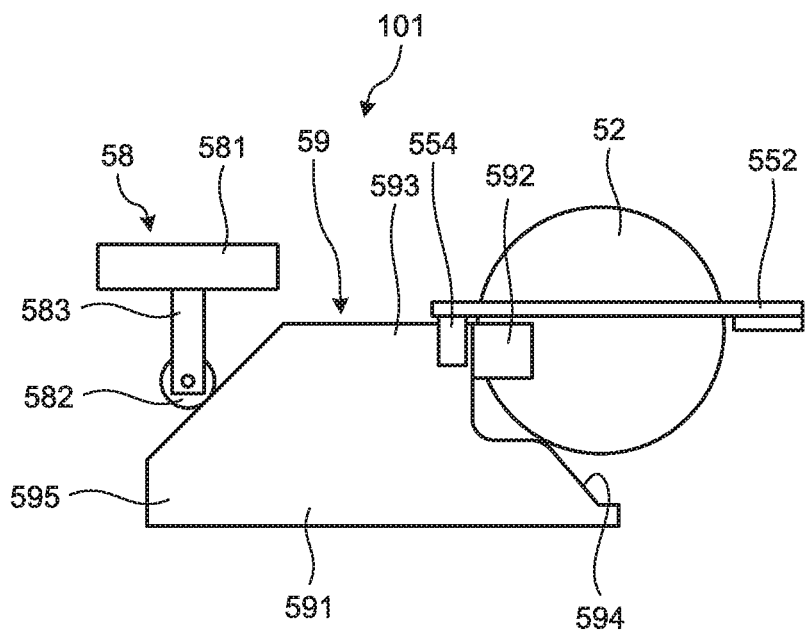
FIG. 14 is a side view illustrating the configuration of the main parts of the input device according to the second embodiment of the present invention.

FIG. 14 is a side view illustrating a configuration of the main parts of the input device according to the second embodiment, illustrating a case where the press button 58 is pressed. When the press button 58 is pressed, the roller 582 moves on the inclined surface of the abutment portion 595. When the roller 582 moves on the inclined surface of the abutment portion 595, a force in a direction orthogonal to the direction of the load, that is, a force in the direction orthogonal to the extraction direction of the track ball 52 is applied to the moving member 59, due to the load applied to the press section 581, thereby moving the moving member 59 toward the track ball 52 side. When the moving member 59 moves toward the track ball 52, the abutment pin 554 moves along the outer surface of the arm 592 in conjunction with the movement of the moving member 59. It is possible to adjust the moving amount of the moving member 59 with respect to the pressing amount of the press button 58 by adjusting the angle of the inclined surface with respect to the moving direction of the moving member 59, on the abutment portion 595.

When the abutment pin 554 moves from the arm 592 to the side surface portion 593 by the movement of the moving member 59, the first opening forming member 551 and the second opening forming member 552 rotate around the rotation shaft 553 in conjunction with the movement. When the first opening forming member 551 and the second opening forming member 552 rotate around the rotation shaft 553, the opening formed by the first opening forming portion 551a and the second opening forming portion 552a is changed from the opening S1 to the opening S2, as described above.

Moreover, when the press button 58 is pressed and the moving member 59 moves toward the track ball 52, the track ball 52 rides on the inclined surface of the inclined portion 594 in conjunction with the movement of the moving member 59. The track ball 52 moves upward with respect to the moving member 59, that is, the amount of protrusion of the track ball 52 from the surface of the main body unit 50 increases, in accordance with the entering amount of the inclined portion 594.

In this manner, after the press button 58 is pressed, the diameter of the opening S2 increases so as not to contact with the track ball 52, which leads to an increase in the amount of protrusion of the track ball 52 from the surface of the main body unit 50. This makes it possible to easily extract the track ball 52 by merely depressing the press button 58.

Moreover, when the track ball 52 is attached onto the main body unit 50, the press button 58 is depressed, and thereafter, the opening formed by the first opening forming portion 551a and the second opening forming portion 552a is expanded (to form the opening S2), and the track ball 52 is dropped into the main body unit 50 from the opening S2. Thereafter, when the pressed state of the press button 58 is released, the inclined portion 594 retreats from the track ball 52 by the self-weight of the track ball 52 or a biasing member such as a coil spring (not illustrated), while the diameter of the opening formed by the first opening forming portion 551a and the second opening forming portion 552a returns to the diameter of the opening S1, and the moving member 59 returns to the normal position.

In the second embodiment described above, the opening S1 formed by the first opening forming portion 551a and the second opening forming portion 552a is smaller than the track ball 52 in diameter when the press button 58 is not pressed, making it possible to prevent the track ball 52 from falling from the main body unit 50. In contrast, by pressing the press button 58, the diameter of the opening formed by the first opening forming portion 551a and the second opening forming portion 552a is changed to the opening S2 so as not to contact with the track ball 52, and the track ball 52 rides on the inclined portion 594, which leads to the increased amount of protrusion of the track ball 52 from the surface of the main body unit 50. In this manner, according to the second embodiment, it is possible to easily attach and detach the track ball 52 to and from the main body unit 50 merely by depressing the press button 58.

Moreover, it is also possible to combine the configuration of the second embodiment with the configurations of the first and second modifications described above.

Embodiments of the present invention have been described hereinabove, however, the present invention is not intended to be limited to the above-described embodiments and the modifications. In this manner, the present invention is not intended to be limited to the above-described embodiments and modifications but may include various forms of embodiments without deviating from the technical spirit and scope of the general inventive concept as defined in the appended claims of this invention. Furthermore, the elements described in each of the embodiments and modifications may be appropriately combined with each other.

In the first and second embodiments, the opening forming member 55 changes the diameter of the opening in conjunction with the movement of the moving member. Alternatively, the opening forming member 55 may be formed of elastically deformable material, and when the track ball 52 protrudes from the main body unit 50, the opening forming member 55 may be elastically deformed by contact with the track ball 52 so as to enable the track ball 52 to be extracted. A slit may be formed in the elastically deformable opening forming member 55. Alternatively, in addition to changing the opening, it is possible to employ an opening and closing mechanism in which the entire opening forming member rotates around an axis parallel to the surface of the main body unit 50 in accordance with the movement of the moving member, thereby avoiding contact with the track ball 52.

Moreover, the above-described first and second embodiments describe exemplary cases of the ultrasound endoscope capable of transmitting and receiving ultrasound and capable of capturing inner portions of the subject with the imaging optical system. The configuration is not limited to this but may also include an endoscope equipped with a ultrasound probe and an imaging optical system, and a capsule endoscope. The medical input device according to the first and second embodiments can be used for operating these endoscopes and probes and for inputting command signals at processing of information obtained by the endoscope and the probe.

It is possible to employ an ultrasound miniature probe that has a small diameter and has no optical system, as the ultrasound probe. In typical cases, the ultrasound miniature probe is inserted into biliary tract, bile duct, pancreatic duct, trachea, bronchus, urethra, and ureter, and is applicable to the examination of the surrounding organs (pancreas, lung, prostate gland, bladder, and lymph nodes, or the like).

It is also possible to employ, as the ultrasound probe, an external ultrasound probe that emits ultrasound from the surface of the subject. The external ultrasound probe is typically used to examine abdominal organs (liver, gall bladder, and bladder), breast (mammary gland, in particular), and the thyroid.

According to some embodiments, it is possible to easily attach and detach the track ball to and from the housing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical input device for receiving an input of a command signal, the medical input device comprising:
    a housing;
    a track ball rotatably disposed in the housing;
    an opening forming member configured to form at least an opening having a diameter smaller than that of the track ball, the track ball being configured to partially protrude through the opening; and
    a moving member having a surface on which the track ball is configured to ride, the moving member being movable in a first direction toward the track ball or in a second direction away from the track ball, the surface being obliquely inclined relative to the first and second directions, the moving member being configured to cause the track ball to ride on the surface such that the track ball moves to further recede from the opening when the moving member moves in the second direction.

2. The medical input device according to claim 1, wherein the opening forming member is configured to vary a diameter of the opening to decrease a diameter of the opening when the moving member moves in the second direction.

3. The medical input device according to claim 2, wherein the opening forming member comprises:
    a first plate having a first arc-shaped concave portion; and
    a second plate having a second arc-shaped concave portion, wherein
    the first plate is pivotably connected on one end side thereof with the second plate such that the first arc-shaped concave portion and the second arc-shaped concave portion face with each other to form the opening.

4. The medical input device according to claim 1, further comprising an actuator configured to generate a driving force for moving the moving member in the first direction or in the second direction.

5. The medical input device according to claim 4, wherein when a predetermined condition related to startup of the medical input device is satisfied, the moving member is moved by driving the actuator.

6. The medical input device according to claim 1, further comprising:
    a detection sensor configured to detect light from a surface of the track ball and output a detection result as information related to rotation of the track ball; and
    a cleaning unit provided on a side surface of the moving member facing the detection sensor and configured to be in sliding contact with a light receiving surface of the detection sensor to remove extraneous matter from the light receiving surface of the detection sensor during movement of the moving member in the first direction.

7. The medical input device according to claim 1, wherein the moving member is configured to cause the track ball to ride on the surface such that the track ball moves to further protrude through the opening when the moving member moves in the first direction.

8. The medical input device according to claim 7, wherein the opening forming member is configured to vary the diameter of the opening to increase the diameter of the opening when the moving member moves in the first direction.

9. The medical input device according to claim 8, wherein the opening forming member comprises:
    a first plate having a first arc-shaped concave portion; and
    a second plate having a second arc-shaped concave portion, wherein
    the first plate is pivotably connected on one end side thereof with the second plate such that the first arc-shaped concave portion and the second arc-shaped concave portion face with each other to form the opening.

10. The medical input device according to claim 8, wherein
    the opening forming member further includes abutment pins on corresponding ones of the first plate and the second plate, and
    the moving member includes arm portions corresponding to the abutment pins of the opening forming member such that the arm portions push the abutment pins to pivotably open the first plate and the second plate to form the opening with the first and second arc-shaped concave portions when the moving member moves in the first direction.

11. A medical input device for receiving an input of a command signal, the medical input device comprising:
    a housing;
    a track ball rotatably disposed in the housing;
    an opening forming member configured to form at least an opening having a diameter smaller than that of the track ball, the track ball being configured to partially protrude through the opening; and a moving member having a surface on which the track ball is configured to ride, the moving member being movable in a first direction toward the track ball or in a second direction away from the track ball, the surface being obliquely inclined relative to the first and second directions, the moving member being configured to cause the track ball to ride on the surface such that the track ball moves to further protrude through the opening when the moving member moves in the first direction.

12. The medical input device according to claim 11, wherein the moving member being configured to cause the track ball to ride on the surface such that the track ball moves to further recede from the opening when the moving member moves in the second direction.

13. The medical input device according to claim 11, wherein:
- the opening forming member is configured to vary the diameter of the opening to decrease the diameter of the opening when the moving member moves in the second direction; and
- the moving member is configured to cause the track ball to ride on the surface such that the track ball moves to further recede from the opening when the moving member moves in the second direction.

14. A medical input device for receiving an input of a command signal, the medical input device comprising:
- a housing;
- a track ball rotatably disposed in the housing;
- an opening forming member configured to form at least an opening having a diameter smaller than that of the track ball, the track ball being configured to partially protrude through the opening; and
- a moving member having a surface on which the track ball is configured to ride, the moving member being movable in a first direction toward the track ball or in a second direction away from the track ball, the surface being obliquely inclined relative to the first and second directions, the moving member being configured to cause the track ball to ride on the surface such that the track ball moves to further protrude through the opening when the moving member moves in the first direction and the track ball moves to further recede from the opening when the moving member moves in the second direction.

* * * * *